(12) United States Patent
Osipchuk et al.

(10) Patent No.: US 9,080,959 B2
(45) Date of Patent: Jul. 14, 2015

(54) HIGH THROUGHPUT SCREENING OF ION CHANNELS

(71) Applicant: Molecular Devices, LLC, Sunnyvale, CA (US)

(72) Inventors: Yuri Vladimirovich Osipchuk, Foster City, CA (US); James Richard Wasson, Los Altos, CA (US); Edward D. Verdonk, San Jose, CA (US)

(73) Assignee: Molecula Devices, LLC, Sunnyvale, CA (US)

( * ) Notice: Subject to any disclaimer, the term of this patent is extended or adjusted under 35 U.S.C. 154(b) by 155 days.

(21) Appl. No.: 13/662,190

(22) Filed: Oct. 26, 2012

(65) Prior Publication Data

US 2013/0143766 A1    Jun. 6, 2013

Related U.S. Application Data

(62) Division of application No. 12/757,499, filed on Apr. 9, 2010, now Pat. No. 8,329,009.

(51) Int. Cl.
| | | |
|---|---|---|
| *G01N 27/327* | (2006.01) | |
| *B01L 3/00* | (2006.01) | |
| *C40B 60/12* | (2006.01) | |
| *G01N 33/487* | (2006.01) | |
| *G01N 33/68* | (2006.01) | |
| *B01L 3/02* | (2006.01) | |

(52) U.S. Cl.
CPC ............ *G01N 27/327* (2013.01); *B01L 3/5085* (2013.01); *C40B 60/12* (2013.01); *G01N 33/48728* (2013.01); *G01N 33/6872* (2013.01); *B01L 3/0275* (2013.01); *B01L 2300/0609* (2013.01); *B01L 2300/0645* (2013.01); *B01L 2300/0829* (2013.01)

(58) Field of Classification Search
CPC ................ B01L 2300/0829; B01L 2300/0645; B01L 3/5085; G01N 33/48728
See application file for complete search history.

(56) References Cited

U.S. PATENT DOCUMENTS

| | | | |
|---|---|---|---|
| 7,429,316 B1 * | 9/2008 | Osipchuk | 204/403.01 |
| 2005/0058990 A1 * | 3/2005 | Guia et al. | 435/5 |

\* cited by examiner

*Primary Examiner* — Karlheinz R Skowronek
*Assistant Examiner* — Lianko Garyu
(74) *Attorney, Agent, or Firm* — Bella Fishman

(57) ABSTRACT

Multi-well plates having contoured well designs allow multi-stage high throughput parallel assaying of ion channels or ion transporters. A well of a multi-well plate has a bottom region that is sized and shaped to simultaneous accommodate a sensing electrode and a pipette for delivering, e.g., test compounds, wash fluid, and optionally ligands. Such multi-well plates may be coupled with an instrument having a pipette head and an electrode plate. Such arrangement facilitates fluidic contact between cells and fluids provided via a pipette. It also facilitates washing of wells with buffers or other wash solutions to allow serial exposure of test cells to various reagents or other stimuli. Generally, the design allows control and test experiments to be performed on the same cell (or cells) in a single well.

20 Claims, 16 Drawing Sheets

HIGH THROUGHPUT SCREENING OF ION CHANNELS

RELATED APPLICATIONS

This application is a divisional application of a co-pending U.S. patent application Ser. No. 12/757,499, filed on Apr. 9, 2010, and titled "High Throughput Screening of Ion Channels," the content of which is incorporated by reference herein in its entirety.

BACKGROUND

Ion channels are membrane proteins that are present in every cell of every living organism. The channels control flow of ions into and out of the cells and thus play a crucial role in cell functioning. Not surprisingly, ion channels constitute a very important class of drug targets. To efficiently develop new drugs, researchers need methods and devices that allow high-throughput screening of compounds (drug candidates) by their action on ion channels. Such drug screening methods and devices require mechanisms for measuring an ion channel's activity and mechanisms for applying compounds to the ion channels.

Ion channels are commonly studied with a technique called patch clamping. This technique involves measuring electrical signals (currents and/or voltages) from individual cells. The cells are arranged in an apparatus such that the magnitude of the electrical signal is directly related to the state of the ion channels, and in particular how much current they allow to pass. Thus, the technique allows direct electrical measurement of ion channel events in living cells, cell membranes and artificial membranes.

The whole-cell and perforated patch configurations of the patch-clamp are widely accepted as providing the best methods of measuring ion channel activity for drug screening. In these methods ion currents flowing through ion channels are measured directly and with high resolution by sensitive current amplifiers.

Unfortunately, current patch clamp instrumentation suffers from a variety of shortcomings, particularly with regard to high-throughput screening of ion channels, and particularly ligand-gated ion channels.

SUMMARY

Certain embodiments disclosed herein pertain to instruments, multi-well plates, and associated well designs allowing high throughput parallel assaying of ion channels and ion transporters. Each well of a multi-well plate has a bottom region that is sized and shaped to simultaneous accommodate a sensing electrode and a pipette for delivering, e.g., test compounds, wash fluid, and optionally ligands (for ligand-gated ion channel assays). Such multi-well plates may be coupled with an instrument having a pipette head and an electrode plate to provide various advantages. First, such arrangement allows immediate measurement of current after application of a ligand through the pipette to facilitate assaying of ligand-gated ion channels. Second, it permits relatively complicated assay protocols in which a single well (and its associated cell) can be used for both the control and test experiments on ion channels, including ligand-gated ion channels. Additionally, some well designs contain contoured features that facilitate fluidic contact between cells and fluids provided via a pipette. This improves washing of wells and cells with buffers or other wash solutions to allow serial exposure of test cells to various reagents or other stimuli. Generally, the design allows control and test experiments to be performed on the same cell (or cells) in a single well. This is particularly useful for ligand-gated ion channels.

In various embodiments, an assembled device includes one or more apertures at the bottom of each well, a plenum below the wells, cells with multiple ion channels sealed to the apertures, a sensing electrodes in the wells beside the cell and a pipette above the cell, and finally, electronics associated with the sensing electrode.

In certain embodiments, the invention pertains to multi-well plates having a plurality of wells, in which at least one well of the multi-well plate has a bottom characterized by the following features: (a) a cell cavity sized and shaped to accommodate a pipette tip, and (b) an electrode pocket sized and shaped to accommodate a sensing electrode. In some cases, the cell cavity and the electrode pocket are arranged to permit simultaneous accommodation of the pipette tip and the sensing electrode. Further, the well bottom may provide a fluidic connection between the electrode pocket and the cell cavity. Typically, the cell cavity includes one or more cell sealing apertures in a bottom surface of the cell cavity.

In various embodiments, the cell cavity comprises a pipette guide, which may have a shape and size for mating with the pipette tip. For example, the pipette guide may be tapered in the vertical direction. In more specific cases, the pipette guide's shape and size prevents a significant fraction of fluid dispensed from the pipette tip, when the pipette is inserted in the guide, from flowing upward and out of the pipette guide. In such designs, and when the well includes fluidic connection between the cell cavity and the electrode pocket, the fluid dispensed from the pipette tip flows primarily into the cell cavity and then through the electrode pocket prior to exiting into an upper region of the well. In embodiments employing an electrode plate (described in more detail below), the pipette guide may be substantially coaxial with a through hole in the electrode plate.

The dimensions of the electrode pocket may depend on various application-specific features, including the size of the wells, the number of wells in the multi-well plate, the size of the electrode, the desired fluidic coupling between the cell cavity and the electrode, and the like. In a specific embodiment, the height of the electrode pocket, in the vertical direction, is between about 0.2 and 2 mm. In another specific embodiment, the center-to-center distance between the electrode pocket and the cell cavity is between about 1 and 5 mm.

Similarly, the dimensions of the cell cavity may depend on application-specific features including those listed for the electrode pocket as well as certain pipette-specific features such as the size and shape of the pipette tips (e.g., the pipette taper), and the splay associated with a pipette head. In certain specific embodiments, the height of the cell cavity, in the vertical direction, is between about 0.2 and 2 mm. Further, the diameter or width of the cell cavity may be between about 0.5 and 2 mm. In certain specific embodiments, the cell cavity has a size and shape such that when a pipette tip engages with the cell cavity, the pipette tip comes within about 0.5 mm or less from the bottom of the cell cavity.

Another aspect of the invention pertains to a patch clamp apparatus that may be characterized by the following features: (a) an electrode plate comprising a plurality of sensing electrodes and a plurality of associated through holes sized and positioned to accommodate pipette tips directed from a pipettor head; and (b) a multi-well plate comprising a plurality of wells, each arranged to align with one electrode and one through hole of the electrode plate. Further, at least one well of the multi-well plate includes a cell cavity sized and shaped to accommodate its pipette tip. Typically, each well of the multi-well plate also includes an aperture for sealing a patch of membrane in the well. Further, the sensing electrodes of the electrode plate are typically arranged to provide one electrode per well of an SBS compliant plate having 96, 384, or 1536 wells. Typically, the electrode plate includes a plurality of contacts for providing electrical connection between the sensing electrodes and associated sensing and recording electronics.

In various embodiments, the at least one well of the multi-well plate includes an electrode pocket sized and shaped to accommodate a sensing electrode of the electrode plate. As with the first aspect described above, the cell cavity and the electrode pocket may be arranged to permit simultaneous accommodation of the pipette tip and the sensing electrode. Also, as described above, the cell cavity may include a pipette guide having a shape and size for mating with a pipette tip directed into the at least one well. Thus, in certain embodiments, the pipette guide may be substantially coaxial with a corresponding through hole in the electrode plate.

Another aspect of the invention pertains to methods of conducting a patch clamp assay in which the method is characterized by the following operations: (a) providing a cell sealed to an aperture on the bottom of a well; (b) exposing the cell to a first solution; (c) measuring a first electrical signal from the cell while or after the cell is exposed to the first solution; (d) delivering fresh solution to the bottom of the well from a pipette inserted in the well; (e) raising the pipette within the well, without removing the pipette, and drawing liquid from an upper region of the well into the pipette; and (f) removing the liquid drawn into the pipette from the well. In various embodiments, the methods additionally include exposing the cell to a second solution to after removing the liquid in (f) and measuring a second electrical signal from the cell while or after the cell is exposed to the second solution. In various embodiments, the first electrical signal provides a control measurement and the second electrical signal provides a test measurement. In further embodiments, measuring a first electrical signal in (c) is performed immediately upon introduction the first solution to the well. Additionally, measuring the first electrical signal may involve detecting the current from a sensing electrode in the well.

The above method embodiments may be practiced with a plates and apparatus as described above. For example, wells used in the method may have a bottom structure defining a cell cavity as described above. In further embodiments, the size and shape of the cell cavity include one or more of the features described above, including features relating to a pipette guide. The method embodiments may also optionally employ a well having an electrode pocket as described above. The dimensions, fluidic coupling arrangement and other features described above may be available when practicing the methods described here.

In yet another aspect, the invention pertains to methods of conducting patch clamp assays on ligand-gated ion channels. Such methods may be characterized by the following operations: (a) sealing a patch of membrane containing at least one ligand-gated ion channel to an aperture on in an assay well; (b) delivering a ligand to the well and measuring an electrical signal resulting from exposing the ligand-gated ion channel to the ligand; (c) pipetting fresh solution to the bottom of the well from a pipette inserted into the well to thereby bathe the patch of membrane with the fresh solution; (d) moving the pipette to a different position in the well and removing old solution containing the ligand from the well; (e) applying a stimulus to the patch of membrane; and (f) delivering the ligand to the well and measuring an electrical signal resulting from exposing the ligand-gated ion channel to the ligand after application of the stimulus. In normal operation in a multi-well plate, the methods will involve repeating the sealing of a patch of membrane in (a) for a plurality of patches in a plurality of wells in a multi-well plate.

In various embodiments, (b) involves immediately measuring the electrical signal upon delivering the ligand to the well. Additionally, the ligand-gated ion channel may be allowed to resensitize after (c) and (d) are complete and prior to performing additional operations. Frequently, the stimulus in (a) involves applying a pharmaceutically active compound or biologic material.

The disclosed LGIC assay methods may be practiced with a plates and apparatus as described above. As with the other method embodiments, wells may have a bottom structure defining a cell cavity and/or electrode pocket as described above. Further, the size and shape (including recited dimensions) of the cell cavity, electrode pocket, and/or pipette guide may be as specified above.

These and other features and advantages will be described in more detail below with reference to the associated drawings.

DESCRIPTION OF A PREFERRED EMBODIMENT

Figure 1A:
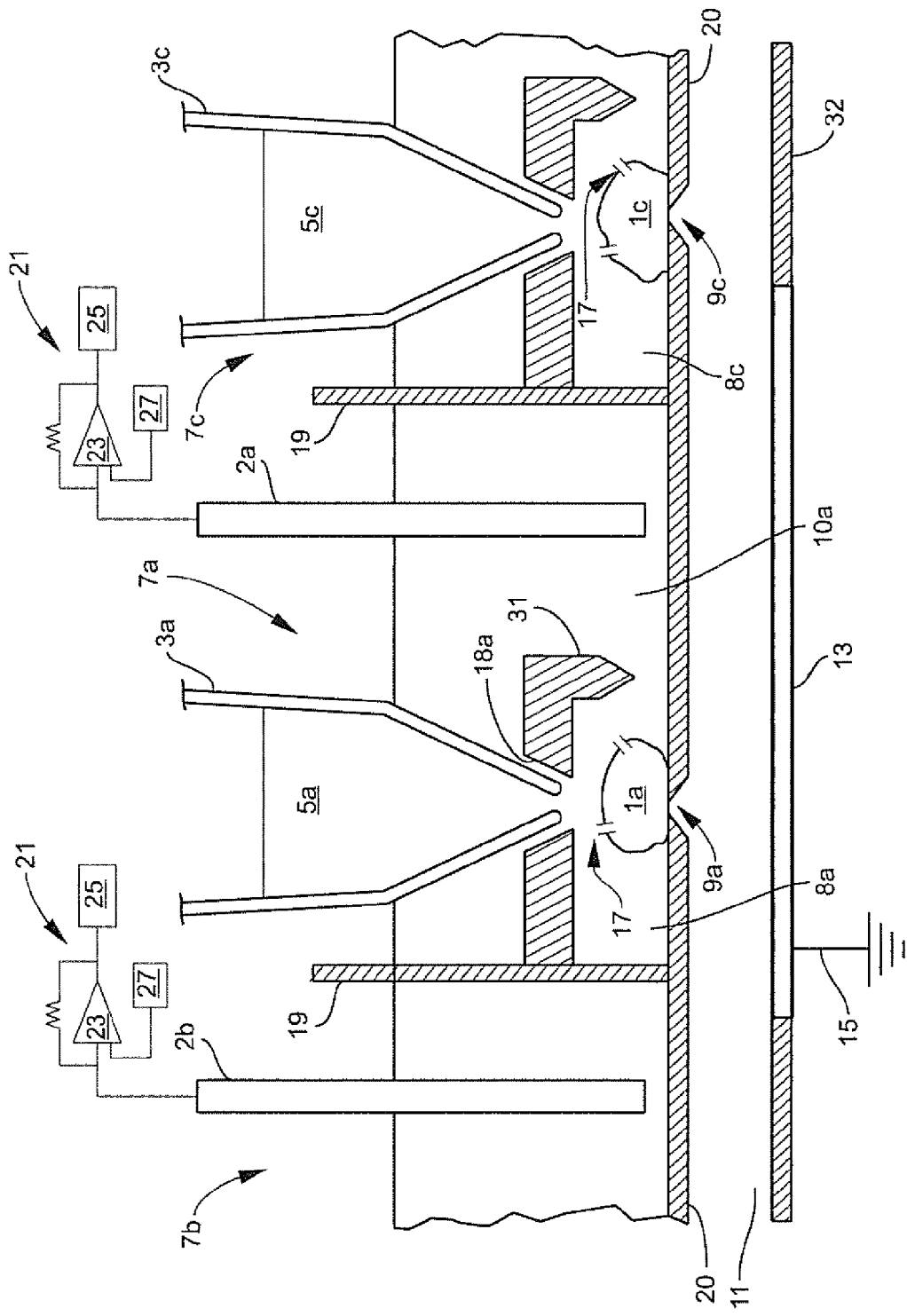
FIGS. 1A and 1B are schematic depictions of a multi-well apparatus for conducting multiple patch clamp experiments in parallel.

Ion channels generally include two parts; the pore (channel) and a switch that regulates the conductance of the pore. Ion channels are passive elements in that once opened, ions flow in the direction of existing electrochemical gradients. Ion transporters are similar in that they are involved in the transport of ions across the cell membrane, however they differ from ion channels in that energy is required for their function and they tend to actively pump against established electrochemical gradients. For convenience, the term ion channel will be used herein to refer to both ion transporters and ion channels.

There are two main types of ion channels: voltage-gated ion channels (VGICs) and ligand-gated ion channels (LGICs). VGICs are activated by changing the electric voltage across the cellular membrane, while LGICs are activated by action of a chemical compound (ligand) on the channel protein. Studying LGICs requires rapid exchange of extracellular solution in the vicinity of patched cells.

An example of an instrument in operational configuration for studying ion channels will now be described with reference to its principal components. These components include a plurality of wells (i.e., more than one well), each with a cell sealed to an aperture, a pipette for delivering and removing fluid from the well, and an electrode for sensing electrical signals in the well. In more specific embodiments that follow, the instrument will be described in terms of a pipette head, a patch plate which contains a plurality of wells, and a separate electrode plate which has multiple electrodes arranged to permit independent sensing in each of the wells of the patch plate. The patch plates and electrode plates of the present invention are not limited to the specific structures presented in the drawings. Some related features of the disclosed embodiments are presented in U.S. Pat. No. 6,488,829 and in PCT Publication PCT/US2005/032044, both incorporated herein by reference in their entireties for their descriptions of patch clamp instrumentation.

FIG. 1A shows, in a schematic format, various features of a multi-well patch clamp apparatus which permits simultaneous patch clamp experiments on multiple cells. In the depicted apparatus, a well 7a is depicted along with partial depictions of adjacent wells 7b and 7c. Each well is bounded by vertical structural members 19 and a bottom horizontal structural member 20. The bottom horizontal member 20 includes a number of apertures including an aperture 9a in well 7a and an aperture 9c in well 7c. During patch clamp experiments, cells are sealed to the individual apertures which permit ionic coupling to the cell interior 8a and 8c. In the depicted example, a cell 1a is sealed to aperture 9a and a cell 1c is sealed to aperture 9c. Below the bottom horizontal member 20 there is a plenum 11, which is designed to hold a fluid, such as an intracellular fluid, during patch clamp experiments. The plenum 11 is bounded on the top by the horizontal member 20 and on the bottom by a parallel horizontal member 32 that includes one or more reference electrodes (e.g., reference electrode 13) which are electrically coupled to ground 15

Each of cells 1a and 1c includes a plurality of ion channels 17 which are evaluated for their response to stimuli in the individual wells of the apparatus. A typical patch clamp assay involves sensing a signal associated with current flowing through the various cells (more particularly current flowing through ion channels in the cells) positioned in the well and having a membrane patch contacting the plenum.

In certain embodiments, the patch clamp experiment is a perforated patch experiment. In this variation of the whole-cell patch clamp experiment, the patch of membrane sealed to the cell aperature is perforated or made permeable to reduce the resistance across the patch of cell membrane in the aperture. Of course, this permeabilization does not affect the conductivity of ion channels but reduces the resistance associated with the lipid components of the membrane in the aperture. The electrical permeabilization of the membrane patch can be induced in many ways. In some embodiments, it is accomplished by contacting the patch with a perforating agent. This may be accomplished by, for example, providing such agent to the solution within the plenum. Examples of suitable perforating agents include certain lipophilic compounds or antibiotics such as amphotericin-B, nystatin, or gramicidin. Such chemicals work by forming chemical pores in the cell membrane that are permeable to monovalent ions such as chloride. Since chloride is the current carrying ion for the commonly used Ag/AgCl electrode, these compounds produce a low resistance electrical access to the cell interior.

In some embodiments, a relatively high voltage is applied to perforate the cell membrane and produce a similar result. In such cases, permeabilization is achieved by applying voltage pulses of sufficient strength and duration that the membrane sealed within the aperture physically breaks down. This is commonly referred to as "zapping."

It should be understood that the invention is not limited to perforated patch embodiments. Other types of patch clamp assays such as whole-cell configurations, which rupture the membrane patch, may also be employed.

In many assays, each stimulus is evaluated for its effect on the ability of the ion channel 17 to pass ionic current. The current is sensed by sensing electrodes such as a sense electrode 2a in well 7a and a sense electrode 2b in well 7b. Such electrodes are typically silver/silver chloride electrodes which provide an electrical connection to sensing circuitry in response to a reversible exchange of chloride ions in the assay solution. The measurement circuit is completed via the reference electrode 13, which may be a second Ag/AgCl electrode.

Typically, though not necessarily, each sense electrode has its own associated sensing electronics. In some cases, however, the multiple electrodes (often in multiple wells) share sensing electronics. As shown, the sensing electronics may comprise various elements indicated collectively by reference number 21. These elements include a high-impedance operational amplifier 23 configured to sense the current flowing in the circuit and a data recording system 25, which is coupled to the amplifier to record and optionally analyze the electrical signals from the well. A high electrical resistance seal between the aperture 9a and the cell membrane permits the current recorded by the amplifier to be dominated by ions flowing through the cell membrane and not by ions flowing around the aperture directly into the well solution. A voltage controller 27 is designed or configured for applying an external voltage between the well electrodes 2b and the reference electrode(s) 13, thereby providing control of the cell's transmembrane voltage potential.

As shown in FIG. 1A, each well includes a separate pipette, e.g., a pipette 3a disposed in well 7a and a pipette 3c disposed in well 7c. At any given time during a patch clamp experiment, the pipettes may hold a particular fluid as appropriate for the current stage of the assay. In some phases, the pipettes are used to deliver fluid to their respective wells and in other phases of an assay, the pipettes are used to remove fluids from their respective wells. In FIG. 1A, the fluids in the pipettes are depicted by the reference numerals 5: 5a in pipette 3a and 5c in pipette 3c.

The bottom of each well contains an internal structural member such as a member 31 having a mid-elevation shelf portion shown in well 7a which is used to at least partially separate a pipette portion of the well from an electrode portion of the well. As explained more fully below, such structures may be employed to define separate cavities with a pipette guide 18a or pockets, such an electrode pocket 10a in well 7a, in different portions of the well. Good fluidic communication between the pipettes and associated cells and electrodes in the individual wells permit simultaneous insertion of a pipette and an electrode in a given well at any point during an assay. This design also facilitates acquisition of data in studies of ligand-gated ion channels.

Figure 1B:
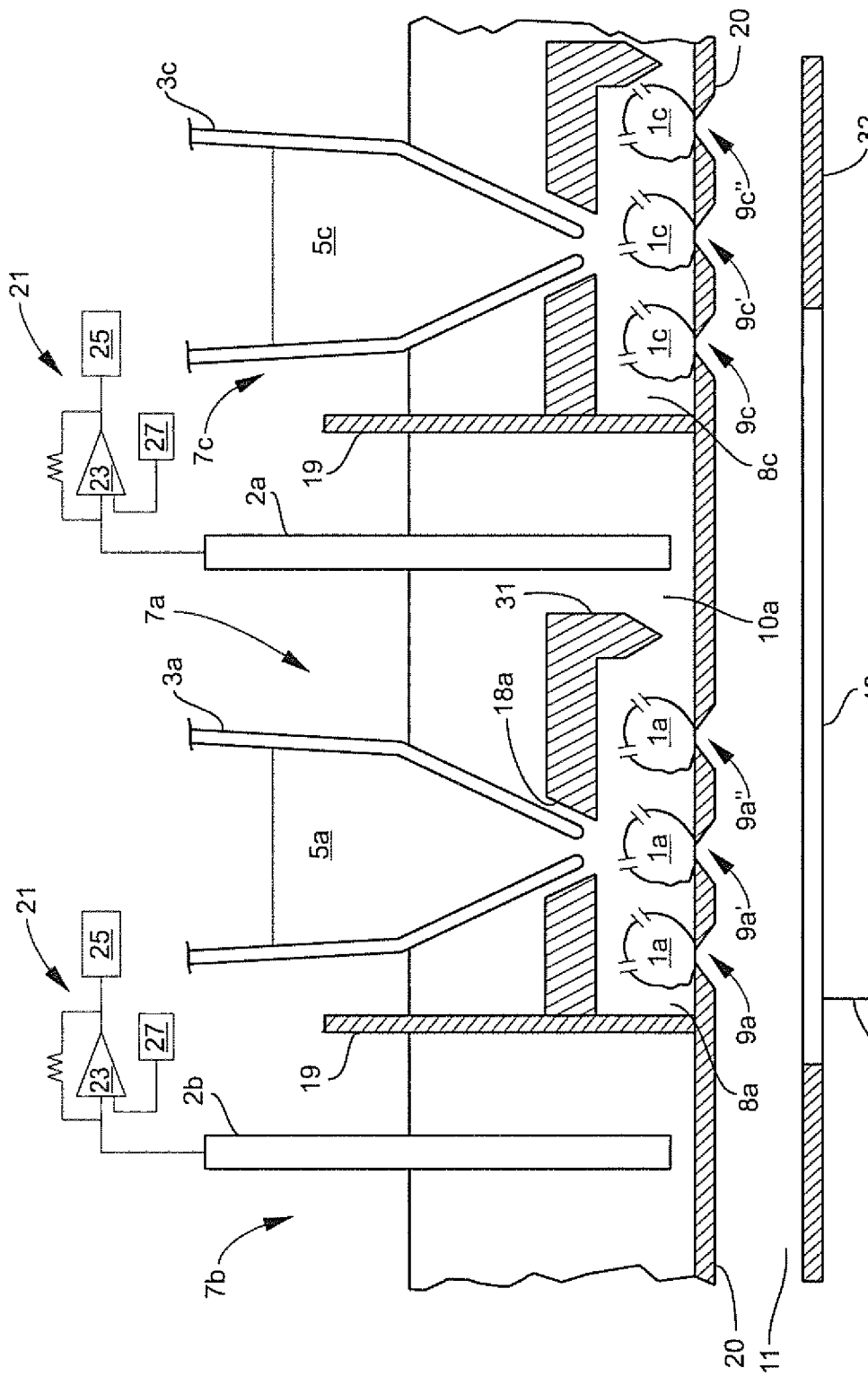

FIG. 1B depicts an embodiment similar to that shown in FIG. 1A except that each of the wells contains multiple apertures: for example, apertures 9a, 9a', and 9a'' in well 7a and apertures 9c, 9c', and 9c'' in well 7c. As shown, each of the apertures is positioned to form a seal with a separate cell. An embodiment employing this design is referred to as a "population patch clamp" or a "parallel patch clamp" (PPC) because it simultaneously considers the effect of a single stimulus on multiple different cells in parallel. In such embodiments, a single well supports multiple cells whose contributions to a signal are collectively sensed. Such designs can provide improved data as they average the contributions of multiple cells, any one of which may behave much differently than the norm. Cell-to-cell variability is often significant; individual cells often exhibit great variability in their response to a particular stimulus. Further details of a PPC assay design are provided in U.S. Pat. No. 8,048,289 issued on Nov. 1, 2011 (see also PCT Publication PCT/US2005/032044), which is incorporated herein by reference in its entirety for its discussion of PPC technology.

It should be understood that the invention is not limited to the study of ion channels in cell membranes. Rather, the membrane under consideration may be from, e.g., any one or more of the following species: cells, vesicles, organelles, cell membrane fragments, and synthetic membranes, any of which include one or more ion channels. In certain embodiments, the membranous sample may be substantially spherically shaped. The portion of the membranous sample outside of the aperture of the partition may be substantially intact.

Figure 2:
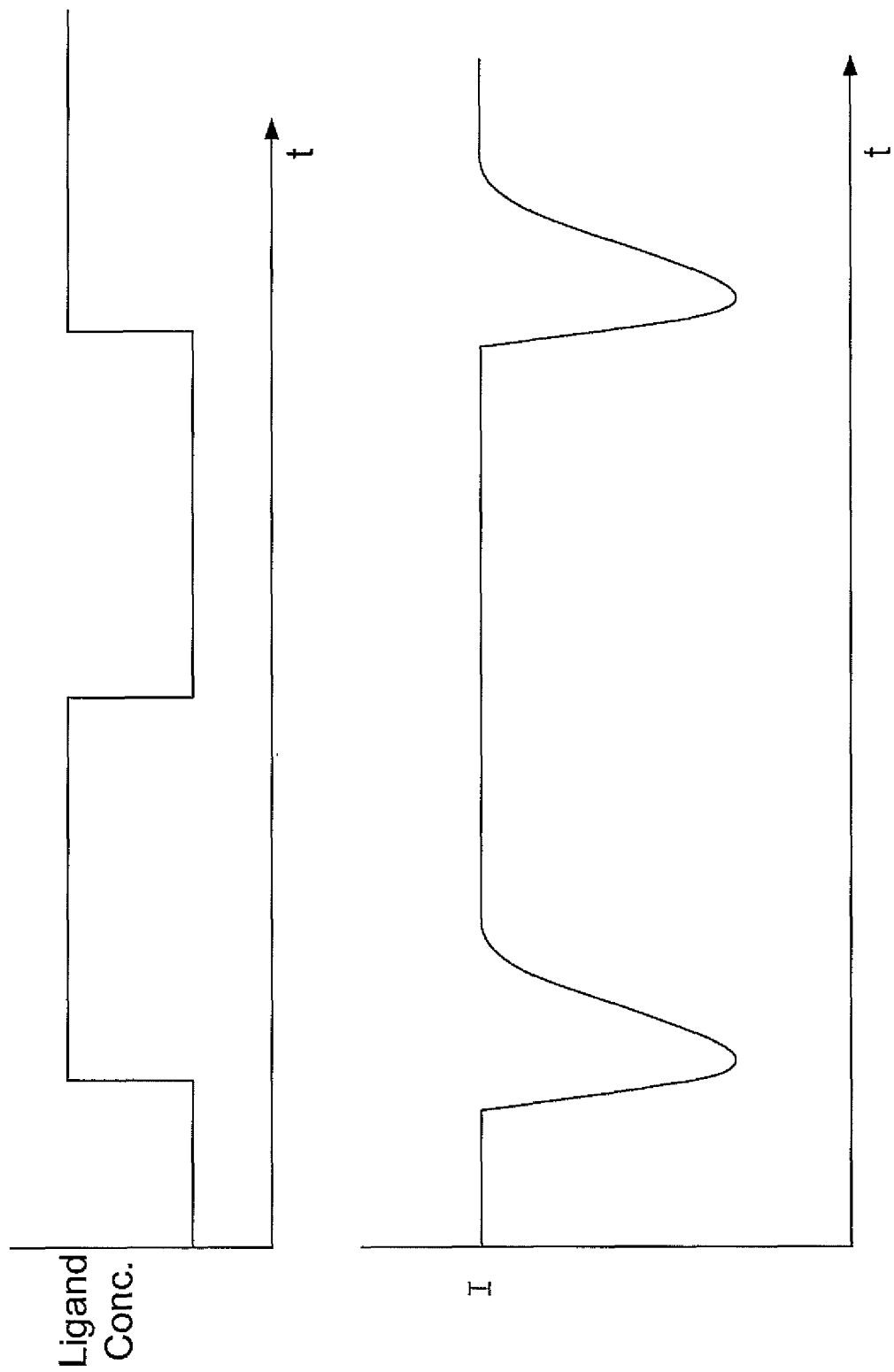
FIG. 2 depicts the response profile of a typical ligand-gated ion channel.

It should be understood that the concurrent presence of the sensing electrode and the pipette in a single well provides various options for assay protocols, particularly protocols appropriate for measuring the effect of drugs on ligand-gated ion channels. FIG. 2 depicts the response profile of a typical LGIC. In the figure, ligand concentration and transient ionic current through the ion channel are plotted along the same time axis (the abscissa axis). Ligand-gated ion channels typically respond to the application of a ligand within a very short period of time, typically less than a second. Very slow acting ligand-gated ion channels respond on the order of one to two seconds. After the response reaches a maximum (as measured by a maximum change in current flow), the channel becomes desensitized. The period of time between the maximum effect of the ligand on the ion channel and desensitization is typically also very short, on the order of a few seconds or less. Therefore, in order to measure the change in current associated with the opening or closing of a ligand-gated ion channel, the electrode (the sensing electrode) and the source of ligand should both be present in the well at the same time. Note that there are some channels with slow or no desensitization.

In some prior designs, only one of the sensing electrode and the pipette could be included in the well at any one time. In these designs, the electrode and pipette could not contact the solution in a given well together, at the same time. To conduct LGIC assays, such systems first pipette the ligand into the well (while the sensing electrode is not in the well), and only later, after the pipette is removed, insert the electrode into the well. Thus, such systems may miss critical early information about the operation of the ion channel.

In the present invention, the electrode and pipette separately and independently, but concurrently, contact the solution in the well. In various embodiments discussed herein, a well may include both an electrode and a pipette at the same time, but at different locations. The pipette has multiple functions in a typical LGIC assay, including delivering the ligand. In the disclosed designs, the sensing electrode can continuously monitor current and provide signal for generating a current trace while the pipette delivers ligand to the well, which immediately impacts the ligand-gated ion channel.

Figure 3:
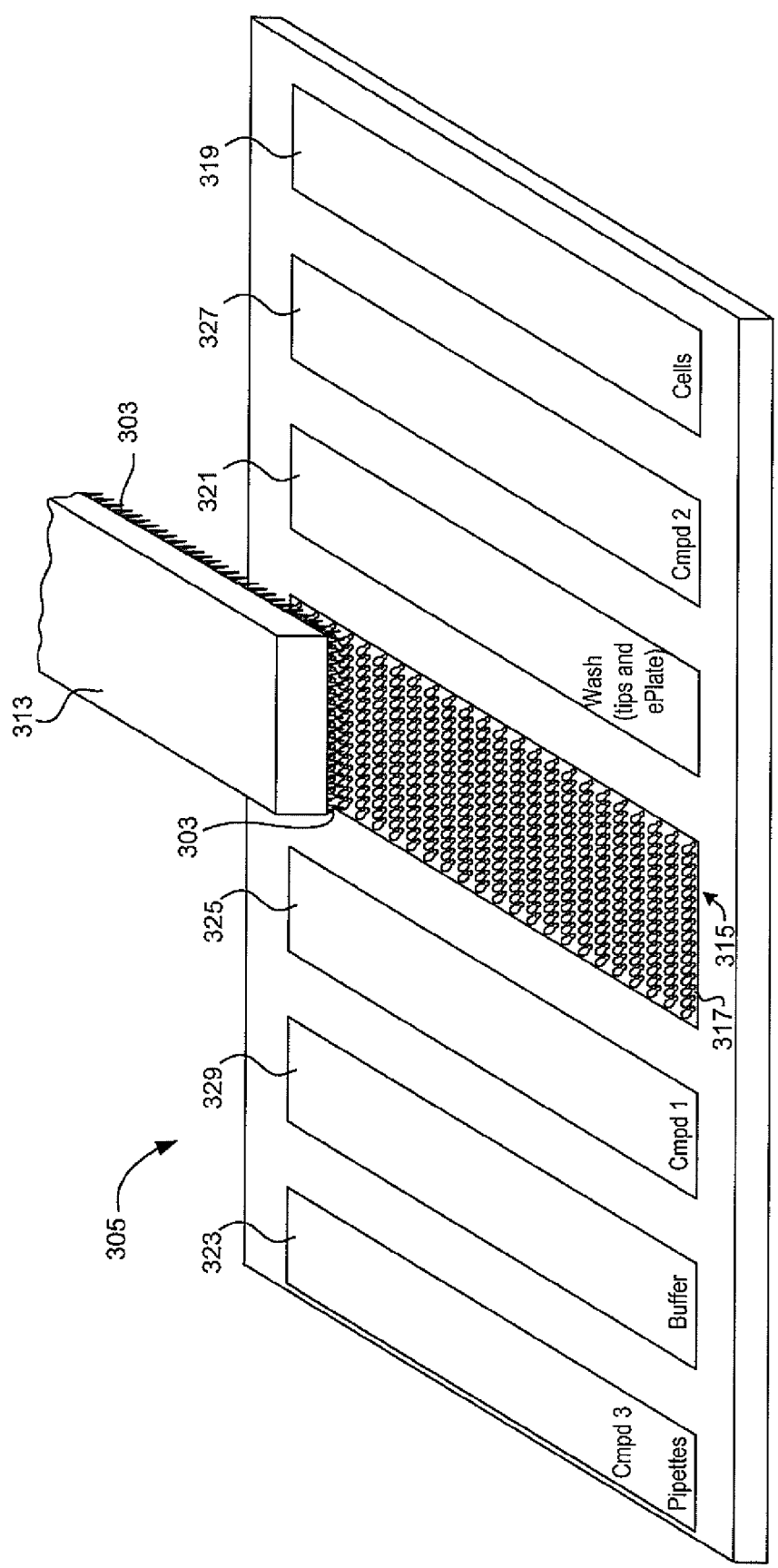
FIG. 3 depicts an instrument including a pipette head and multi-well test station for performing high throughput patch claim assays.

FIG. 3 is a top view of a particular apparatus for performing high throughput patch clamp assays. As shown, various stations are available for providing reagents, cells, wash solutions, etc. to a multi-well plate. The depicted apparatus includes a pipette head 313 with multiple pipettes 303 installed, which pipette head can move between a test region 315, where a multi-well patch plate and associated electrode plate 317 reside, and other stations straddling this test region, which other regions include a cell reservoir 319, a wash solution reservoir 321, a pipette cleaning station 323, a ligand reservoir 325, and a test compound or drug station 327. Additionally, the apparatus may include a buffer station 329 containing, e.g., fresh extracellular solution for delivery to the wells. All of these various stations are provided on a chassis or table mounted platform 305 over which the pipette head can move laterally and vertically under the control of appropriate operational logic, which may be provided by an appropriately programmed computer and/or hard coded logic.

Specifically, the pipette head may be a robotic multi-channel pipettor head, with disposable or non-disposable tips, such as a standard multi-channel fluidics pipettor (an example of such a pipettor is a pipettor used in the FLIPR® (Fluorescence Imaging Plate Reader) instrument available from Molecular Devices, LLC of Sunnyvale, Calif.). Disposable plastic or glass pipettes are typically used. The fluidics head may be mounted on an X-Y-Z moving actuator. The actuator moves the fluidics head in such a way as to allow pipettes to line-up with openings above the wells and to reach through these openings inside the wells of a patch plate mounted in the test region. Preferably the fluidics head is able to both aspirate fluid from the wells and dispense fluids into the wells.

In general, high throughput implementations described herein employ robotics, data processing and control software, liquid handling devices, and detectors. High-throughput screening allows a researcher to quickly conduct hundreds, thousands, or millions of biochemical, genetic or pharmacological tests on ion channels. Advanced systems permit automated application of reagents and wash solutions in parallel to high-density multi-well plates.

Figure 4A:
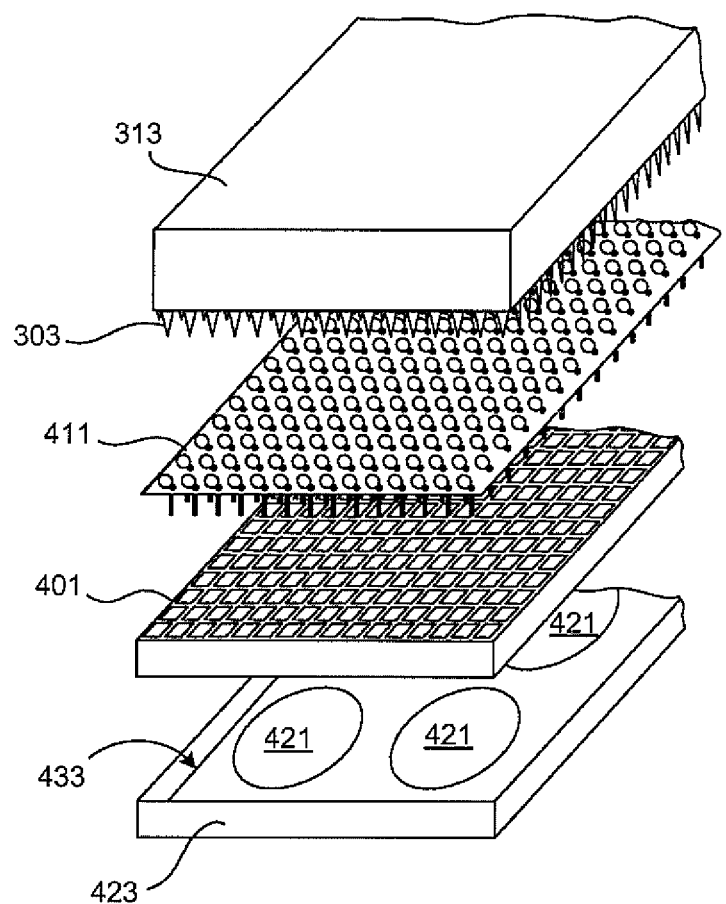
FIG. 4A presents an exploded view of a multi-well patch clamp region including a plenum, a patch plate, an electrode plate, and a pipette head.
Figure 4B:
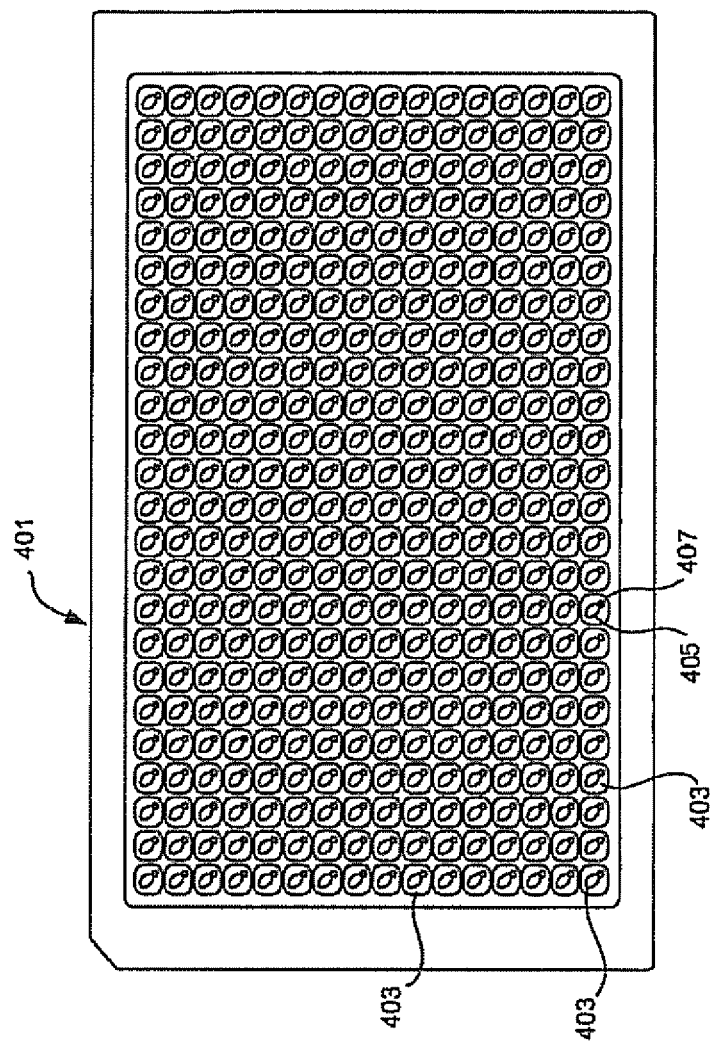
FIG. 4B is a bottom view of patch plate 401 in accordance with certain embodiments.

FIG. 4A presents an exploded view of a test region (such as test region 315 of FIG. 3). The exploded view shows a plenum 423 comprising a plenum reservoir 433, with the patch plate 401 above it, an electrode plate 411 above the patch plate, and finally, a pipette head 313 above the electrode plate 411. Note that plenum 423 includes multiple disk-shaped reference electrodes 421, such as Ag/AgCl electrodes coupled to ground, and mounted to a bottom surface of a plenum compartment 413. The various components of this test region will now be described individually, and in more detail FIG. 4B is a bottom view of patch plate 401 in accordance with certain embodiments. The patch plate in the depicted figure includes 384 separate wells 403 arranged in an array. Of course, plates with different numbers of wells can be used, such as patch plates with 1536 different wells or 96 different wells. By using a patch plate, with its large number of wells, currents from many cells can be measured concurrently, simultaneously and independently, which allows rapid characterization of compounds or other stimuli applied to the cells. Each cell (or multiple cells) is separated from the rest of the studied cells by placing that cell (or cells) in a separate well of the patch plate.

The outside dimensions and shape of the patch plate are, in certain embodiments, compatible with the SBS standard (Society for Biomolecular Screening) for multi-well plates to facilitate handling by standard robotic equipment. As depicted in FIG. 4B, each well 403 includes a cell cavity 405 in the lower left region of the depicted well and an electrode pocket 407 disposed to the right of the cell cavity. Further details of suitable designs for wells 405 will be provided in the description that follows.

In certain embodiments the patch plate is assembled from two parts. One of the parts is injection molded from an inert, biocompatible and electrically insulating plastic, such as polycarbonate, polystyrene or any other suitable material. This part defines the top and side walls of the wells. It may also define the pipette and electrode pockets or cavities as described below. In a specific example, the bottom of each well contains one or two relatively large apertures (e.g., about 0.25 to 5 mm, or about 1-2 mm, or in a specific case about 1.5 mm in diameter). One of these apertures should be sized and shaped to accommodate a pipette tip. If two apertures are employed, the second should be sized and shaped to accommodate a sensing electrode. In some embodiments, the electrode diameter is about 0.5 to 2 mm (e.g., about 1 mm).

The second part of the patch plate is a thin film of electrically insulating material, such as glass or plastic film, for example a polyimide film such as Kapton (poly(4,4'-oxydiphenylene-pyromellitimide)) film. Other suitable polymers include polyethylene terephthalate (PET—e.g., Dupont Mylar™), polycarbonate, polypropylene, and polyethylene. The film is bonded to the bottom of the molded part, covering the aperture. The film contains many smaller apertures, one or more per each well. In one embodiment, the bottom of each well of the patch plate contains a single through-hole aperture, with at least one dimension of the aperture (typically the diameter of the hole) smaller than the dimension of the cells (e.g., about 1-10 micrometers). Typically the smallest diameter of the hole is approximately 2 micrometers. In another embodiment, each well of the patch plate contains a plurality of the through-hole apertures (a typical number of apertures in each well is 64). This is a PPC configuration, which was identified in the embodiment of FIG. 1B.

In some cases, the patch plate is hermetically attached or otherwise mounted to the plenum, such that the apertures at the bottom of each well connect the well and the plenum compartment. The hermetic seal may be provided by an elastic gasket and a frame (e.g., a metal frame) that compresses the patch plate to the gasket. After mounting the electrode plate, the plenum is filled with an intracellular buffer solution. The wells are filled with extracellular buffer solution. As mentioned, the plenum further contains one or more silver/silver chloride (Ag/AgCl) electrodes connected to electrical zero reference (electrical ground).

Figure 4C:
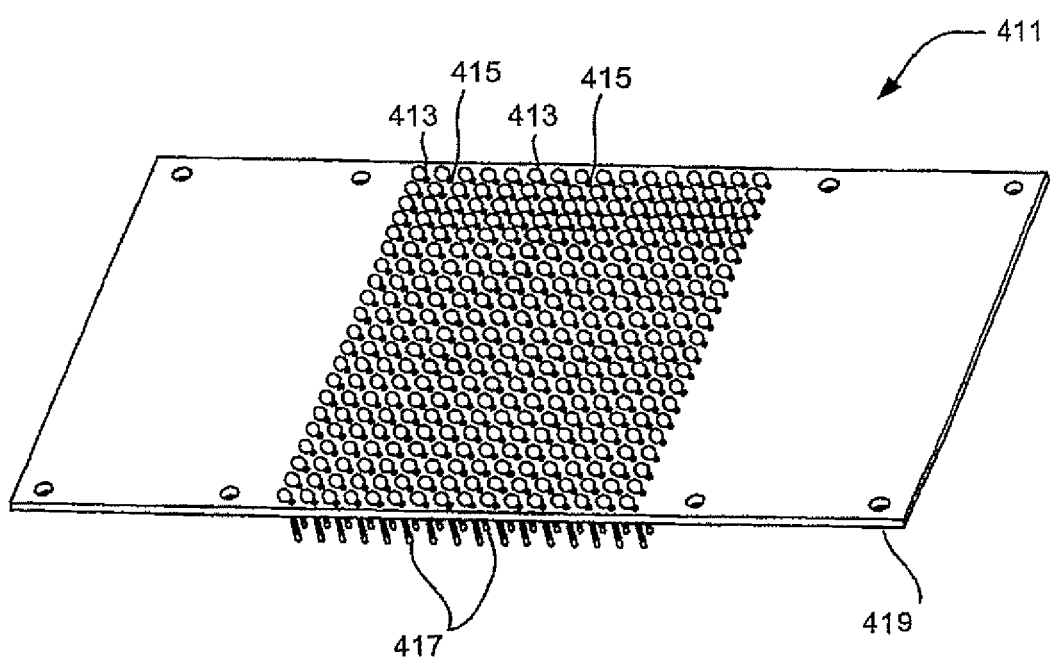
FIGS. 4C through 4E depict an embodiment of an electrode plate suitable for use with the patch plate depicted in FIG. 4B.
Figure 4D:
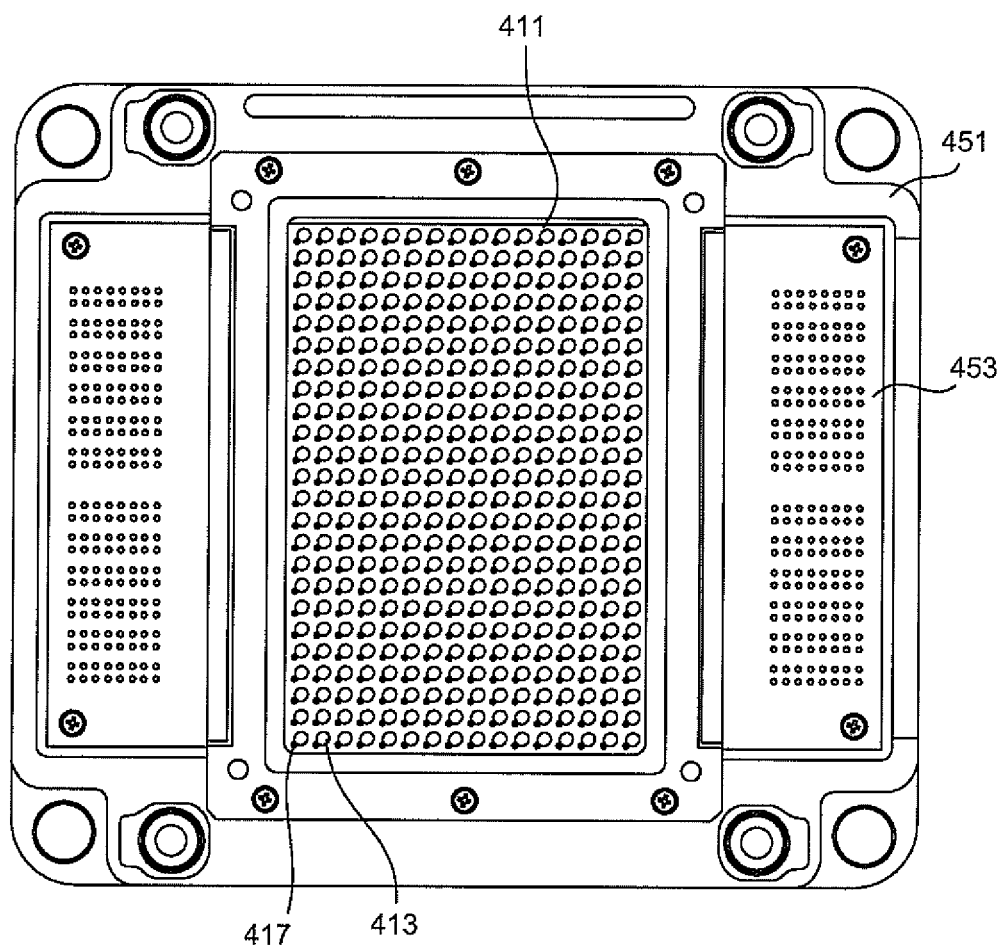
Figure 4E:
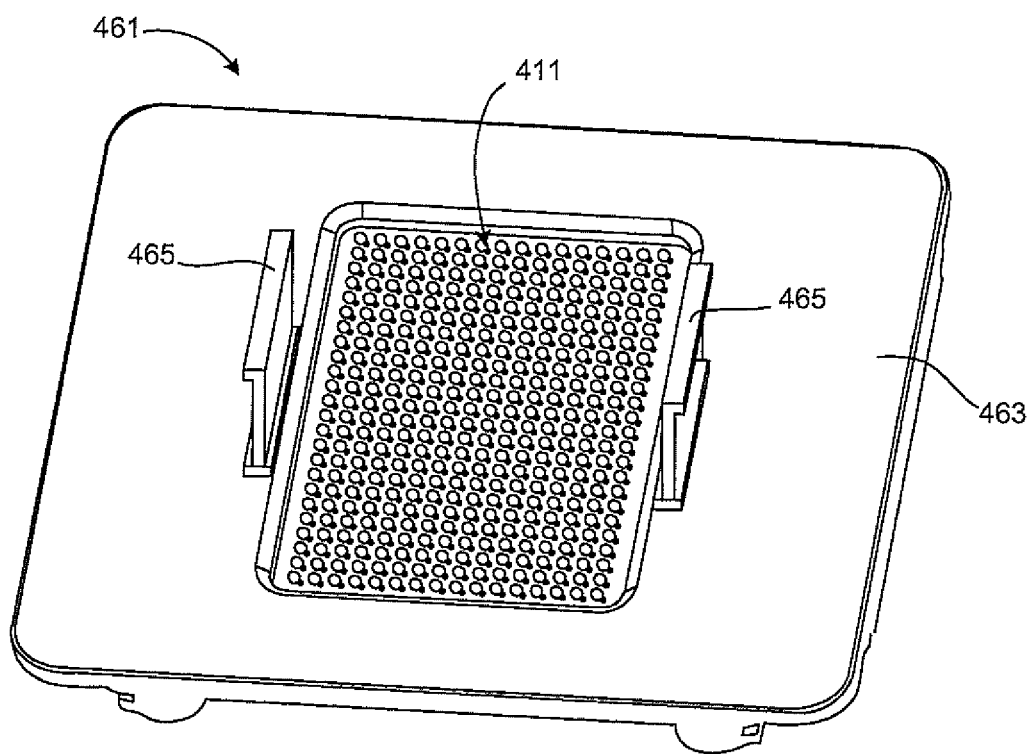

FIGS. 4C through 4E depict an embodiment of an electrode plate suitable for use with the patch plate 401 depicted in FIG. 4B. As shown in FIG. 4C, the electrode plate 411 includes a substrate 419, such as a printed circuit board substrate, an array of electrodes 417 having tips of electrodes 415 and an associated array of pipette through holes 413. For each separate well in the corresponding patch plate there is an associated electrode 417 and an associated through hole 413 being in contact with an associated tip of electrode 415. Thus, the electrodes 417 and through holes 413 are sized and spaced for the patch plate. In a specific embodiment, there electrodes are spaced to provide one electrode for every well of a 384-well configured SBS compliant plate. In other embodiments, the electrodes are spaced to provide one electrode for every well of a similarly compliant 96-well or 1536-well plate.

The through holes 413 are arranged to permit access of a separate pipette for each well of patch plate 401. Further, in the depicted example, the through holes 413 are positioned with respect to electrodes 417 so that one pipette tip and one electrode 417 are co-located in each well.

In some cases, substrate 419 is a printed circuit board (PCB) onto which the array of electrodes is attached, e.g., soldered. In a specific embodiment, each electrode is shaped as, for example, a cylinder, approximately 1 mm in diameter, and made from either silver or some other metal (such as steel) plated with silver. Each electrode is covered by electrically insulating coating (e.g., TEFLON®, PTFE, polytetrafluoroethylene) except for the most proximal part (bottom) of the electrode, which remains uncoated by masking during the coating process. The top part of the electrodes is soldered into the substrate, the bottom, uncoated by Teflon part (approximately 1 mm long) is coated with silver chloride. As indicated, the substrate further contains an array of pipette openings 413, each hole at a specified distance (e.g., about 2 mm) from each electrode. Examples of certain electrode plate embodiments suitable for use with the invention are further described in U.S. Pat. No. 8,048,289 (see also PCT Publication PCT/US2005/032044), previously incorporated by reference.

In the embodiment depicted in FIG. 4D, the electrode plate 411 is part of a larger structure having an outside area 451, which may be a frame, beyond the area occupied by the electrode array, and containing electrical connections 453, such as gold-plated pads for connecting individual electrodes with monitoring and control circuitry in the chassis. FIG. 4D is a bottom view of the electrode plate and frame structure with through holes 413 and electrodes 417 shown. In some cases, the electrical connections 453 are pins or springs such as spring-loaded pogo-pin electrical connectors. In such cases, when installed in the apparatus, the spring-loaded pogo-pin connectors mate with contacts on the platform adjacent the test region, providing electrical connection between the amplifiers and/or voltage control circuitry (mounted to device's chassis) and the sense electrodes of the electrode plate. In alternative embodiments, pogo-pin connectors are provided on the instrument's chassis and mating pads are provided on the electrode plate. Regardless of the structure of the contacts on the electrode plate, each contact 453 is connected by a trace wire (not shown) on the substrate to its respective sense electrode.

In the depicted embodiment, the assembly's outer region 451 is an underlying portion of a frame such as a metal frame, which provides rigidity to the resulting assembly. Additionally, the frame may contain features which facilitate clamping the electrode plate to the instrument. FIG. 4E shows such frame and electrode plate assembly 461 (view from above) including a frame 463, which in turn includes handles 465 to facilitate manual installation and removal of the electrode plate.

The electrode plate together with the frame is mounted (e.g., clamped) to the instrument in such a way that the electrodes engage with the patch plate. For example, when the frame and electrode plate assembly is placed on a mating surface of the test surface, the electrodes of the plate insert into corresponding wells of the patch plate providing electrical connection between the fluid in the wells and the electrodes (typically one electrode per well). The array of contacts on the outer region of the frame underside concurrently line up with and makes electrical connection with corresponding contacts of the chassis. These corresponding contacts may be provided on mating component (e.g., a region of the platform or chassis straddling the test region).

As indicated, the instrument additionally contains current-sensing amplifiers, preferably one amplifier per each well of the patch plate. The instrument contacts are connected to the current amplifiers' inputs, such that when the electrode plate is installed on the instrument the electrodes of the electrode plate connect the fluid in each well with the amplifier inputs.

Figure 5A:
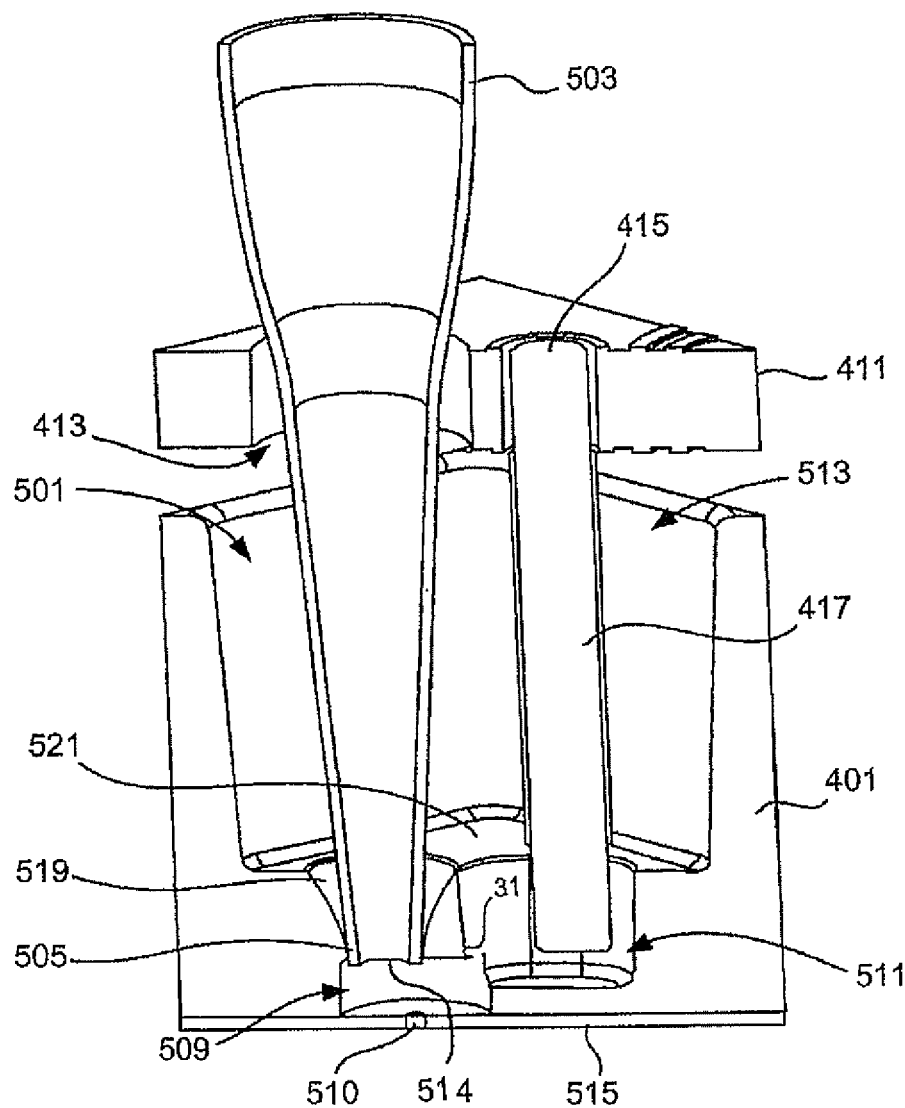
FIG. 5A presents a diagonal cross-section through a single well in a patch plate.

FIG. 5A shows a diagonal cross-section through a single well 501 in a patch plate 401. It also shows an electrode plate with an associated electrode 417 disposed in well 501. Additionally, it shows a pipette 503 extending through a through hole 413 in electrode plate 411 and into well 501. Well 501 includes an opening or top 513 and a bottom 515. Proximate the well's bottom 515, there is a contoured region including a cell cavity 509 and an electrode pocket 511. In the depicted embodiment, the cell cavity 509 extends to very bottom of well 501 while the electrode pocket 511 does not. The cell cavity 509 and electrode pocket 511 are fluidically coupled to one another near their respective bottoms.

The cell cavity 509 has as its bottom, the bottom sheet or membrane 515 of the well. Within the cell cavity 509, and through bottom membrane 515, there is an aperture 510 to which a cell under investigation seals during assaying. In a parallel patch clamp design, there will be multiple apertures 510 in the bottom of cell cavity 509.

As shown, the member 31 forms a top of cell cavity 509, which opens at a through hole 514 into the upper portion of well 501 at a mid-elevation shelf defined by a relatively flat substantially horizontal region 521. Directly below region 521, cell cavity 509 is defined by a pipette guide 519 which, in the depicted embodiment, is a generally conical or funnel-shaped pipette catching feature designed to direct or position the pipette tip 505 into a location proximate aperture 510. By positioning the tip of an entering pipette at the through hole 514 to the cell cavity, the pipette guide ensures consistent and direct fluidic communication between the pipette tip and cells on aperture 510. Typically, pipette guide 519 is substantially coaxial with the corresponding opening (pipette through hole) in the electrode plate substrate.

As mentioned, the instrument may include a robotic pipettor head with multiple pipettes, such as disposable plastic pipettes. The fluidics head aligns the pipettes with openings in the electrode plate allowing the pipettes to reach through these openings and inside the wells of the patch plate. When a pipette is inserted into the well by the fluidics robot, the pipette is captured by a pipette guide, which registers the tip of the pipette. Multichannel fluid pipettors usually exhibit certain positional errors (splay) of the tips of the pipettes, especially with disposable plastic pipettes, at least because the pipette tips are dimensionally imprecise. In the absence of the pipette guide this splay results in variability of the distance between the tip orifice of the pipettes and the cells in the different wells, causing undesirable variability of fluid exchange. The pipette guide centers the tip of the pipette in the well, reducing this variability.

As indicated, the bottom of well 501 includes two openings to the upper region of the well, one serving as a pipette guide, and the other serving as a pocket for the electrode (to the right in FIG. 5A). The cell cavity and electrode pocket promote fluid exchange at the very bottom of the well, where the patched cell(s) are located. In certain embodiments, the pipette guide 519 forms a tight (or substantially tight) seal with the pipette tip 505. This provides a clearly defined flow path for fluid delivered from the pipette. Specifically, when the fluid is dispensed into the well from the pipette tip, the fluid flows through the cell cavity 509, thus being directly applied to the cells. The fluid then flows into the electrode pocket 511 and exits into the well above.

This design facilitates replacement of used or old fluid in wells when transitioning from one phase of a patch clamp experiment to the next. For example, the design permits the replacement of ligand containing solution with fresh ligand-free extracellular buffer or wash solution when transitioning between a control phase and a test phase of an assay. Generally, the fluid entering the cell cavity through the pipette guide replaces the fluid surrounding the cell (or cells). The process of delivering fluid from a pipette in the cell cavity flushes the old fluid, and possibly some excess of the new fluid, which flows through the electrode pocket and then into the top part of the well. Thus, the pipette guide, the cell cavity and the electrode pocket create a flow-through channel in the well. Flowing the liquid through this channel results in efficient and fast fluid exchange in the vicinity of the cell or cells. In certain embodiments, the size and shape cell cavity, the electrode pocket and the fluidic connection therebetween define a microfluidic flow passage.

Figure 5B:
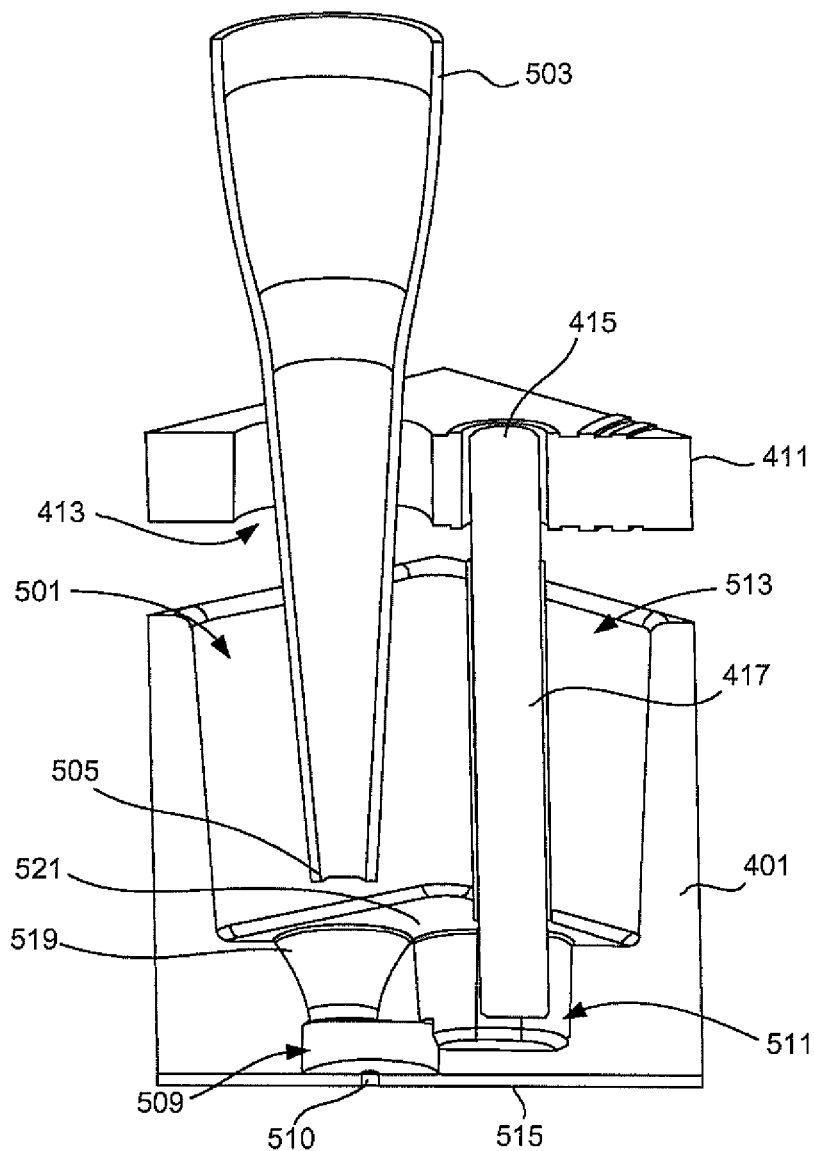
FIG. 5B depicts the well of FIG. 5A but with the pipette raised to an intermediate elevation in the well to draw solution from upper regions of the well.

In various embodiments, the fluidics head is able to dispense fluids into wells and/or aspirate the fluid from the wells of the patch plate (by, e.g., creating a vacuum when the pipettes are raised within the wells 501). As with FIG. 5A, FIG. 5B depicts well 501 together with the electrode plate electrode 417 and pipette 503. However, in this depiction, pipette 503 has been raised to an intermediate elevation in well 501. Concurrently with or shortly after raising the pipette 503, a mechanism is triggered to aspirate or otherwise draw in some fluid from the upper regions of well 501, thereby allowing further cleansing of the cell or cells under consideration in the assay. In certain embodiments, the mechanism is a conventional fluid aspiration mechanism such as a set of moving syringe plungers associated with the pipettes. Note that the pipette tip is lifted up to a position where it draws in the liquid from the top portion of the well, i.e., where the excess or "dirty" liquid has accumulated, leaving behind the "clean" liquid in the bottom cell cavity. This lifting/aspiration process, when coupled with prior delivery of wash or new reagent solution to the well, provides a particularly effective and efficient way of replacing used solution with fresh solution.

Figure 5C:
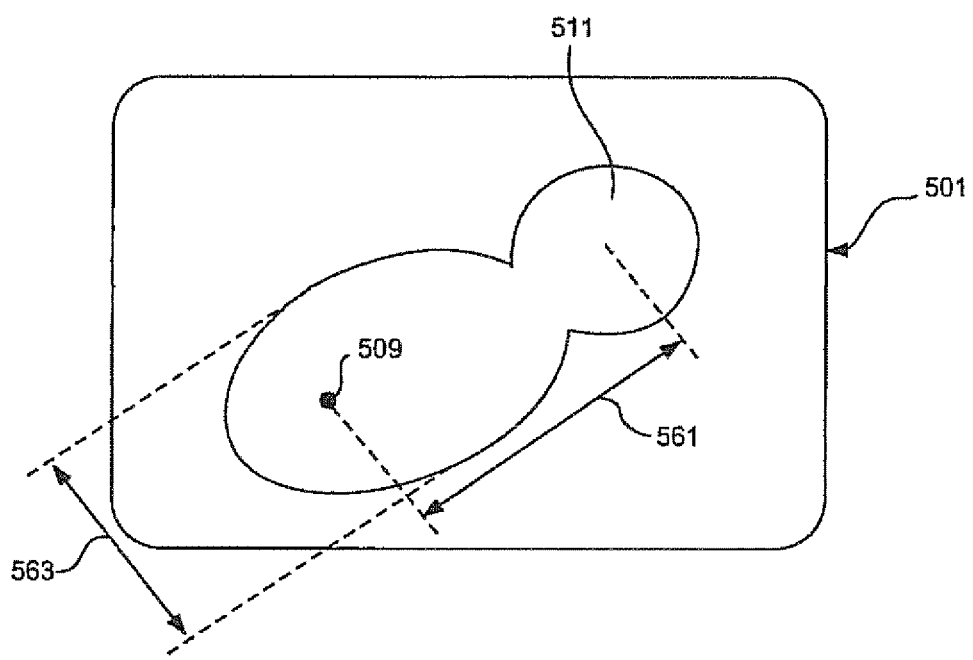
FIG. 5C is a top view of a well having a cell cavity and an electrode pocket.

FIG. 5C is a top view of well 501 taken from a similar perspective as depicted for the entire patch plate in FIG. 4B. As shown in FIG. 5C, well 501 includes the cell cavity 509 together with aperture 510 in the lower left region of well 501, and also includes the electrode pocket 511 above and to the right of the cell cavity. Also, as indicated, cell cavity 509 and electrode pocket 511 intersect and are in fluidic communication. In other words, the electrode pocket and cell cavity touch or overlap when viewed from above. The center-to-center distance between electrode pocket 511 and cell cavity 509 is depicted by a line 561. In certain embodiments, this distance is between about 1 and 4 mm, and more specifically between about 1.5 and 3 mm, typically about 2 mm. The cross sectional area of the fluidic connection between the cell cavity and the electrode pocket may be, for example, about 0.1 to 10 $mm^2$, or more specifically about 1 to 2 $mm^2$.

In certain specific embodiments, the well has an open upper region, which is to say that the upper region of well does not contain chambers, baffles or other internal features. The lower regions of the well, however, are contoured to include certain features, typically at least a cell cavity. Often the contoured lower region of the well will also include an electrode pocket and a fluidic connection between the electrode pocket and cell cavity, which connection is provided proximate the bottoms of the pocket and the cavity. While the figures presented herein depict the shape defined by the outer walls of the well (when viewed from above) to be generally square, this need not be the case. In certain embodiments, the shape is generally rectangular, circular, elliptical, etc.

Generally, the electrode pocket is sized and shaped to accommodate the sensing electrode with relatively little excess volume beyond that necessary to accommodate the electrode. In certain embodiments, the pocket is generally cylindrical in shape, although it may be polygonal, elliptical, oval, etc. The shape will generally match that of the sensing electrode. In various embodiments, the height of the pocket (in the vertical direction) may be at most about 5 mm, typically between about 1 and 3 mm. In some cases, the principal width or diameter of the pocket may be between about 0.25 and 5 mm, and often between about 1 and 3 mm.

As explained, the cell cavity may open into the upper portions of the well via a pipette guide. The total vertical depth of the cell cavity, including the pipette guide if present, is typically at least about 2 mm, and in specific embodiments between about 0.5 and 5 mm. In typical examples, the principal diameter or width of the cell cavity will be between about 0.5 and 5 mm, and more specifically between about 1 and 2 mm. The shape of the cell cavity may be, for example, round, square, rectangular, elliptical, triangular, or other polygonal shape. In certain embodiments, the cell cavity width or diameter is illustrated by arrow 563 in FIG. 5C. Aside from the pipette guide, the shape and dimensions of the cell cavity typically will not vary significantly along its vertical extent.

Regardless of whether a pipette guide is employed, the cell cavity may be constructed such that when a pipette tip engages with the cavity, the tip comes within about 0.5 mm or less from the aperture(s) at the bottom of the cavity. This facilitates washing of cells with wash or buffer solution from the pipette. In some cases, the vertical distance occupied by the cell cavity is between about 10 and 50% of the total height of the well. Further, the volume occupied by the cell cavity may be between about 0.5 and 5% of the total volume of the well. In specific examples, the total volume of the cell cavity is between about 500 and 2000 nanoliters.

The pipette guide, when present, generally has a shape and size for mating with the pipette tip; that is the guide is sized and shaped to circumferentially engage the pipette tip when the pipette is in a final lowered position. Therefore, it will generally have a taper, such as a conical shape or a pyramidal shape. However, in some embodiments, it may also have a blunt shape such as an untapered cylindrical or rectangular shape.

Functionally, the pipette guide may, by virtue of its shape and size, prevent a significant fraction of fluid dispensed from the pipette tip, during normal operation, from flowing upward and out of the pipette guide. When the well also has a fluidic connection between the cell cavity and the electrode pocket, fluid dispensed from the pipette tip positioned in the pipette guide may flow primarily into the cell cavity and then through the electrode pocket prior to exiting into upper regions of the well. In certain embodiments, the pipette guide is between about 0.1 and 5 mm long, and in more specific embodiments, between about 1 and 2 mm long. The diameter or width of the pipette guide at its lower extent may be between about 0.1 and 3 mm in certain designs. More specifically, this diameter or width may be between about 0.5 and 2 mm.

In accordance with certain embodiments of the invention, various methods and protocols are provided for performing patch clamp experiments in parallel using a multi-well system. Certain of these protocols employ distinct sequences for ligand-gated ion channels and voltage-gated ion channels. Some sequences permit performance of both control and test experiments in a single well on the same cell or cell population contained in that well. A few non-limiting sequences will be described with reference to FIGS. 6A-6D. At times, these methods will be described with reference to a patch plate or other apparatus described above. It should be understood, however, that the invention represented by these methods is not, unless otherwise noted, limited to the particular apparatus described above.

Figure 6A:
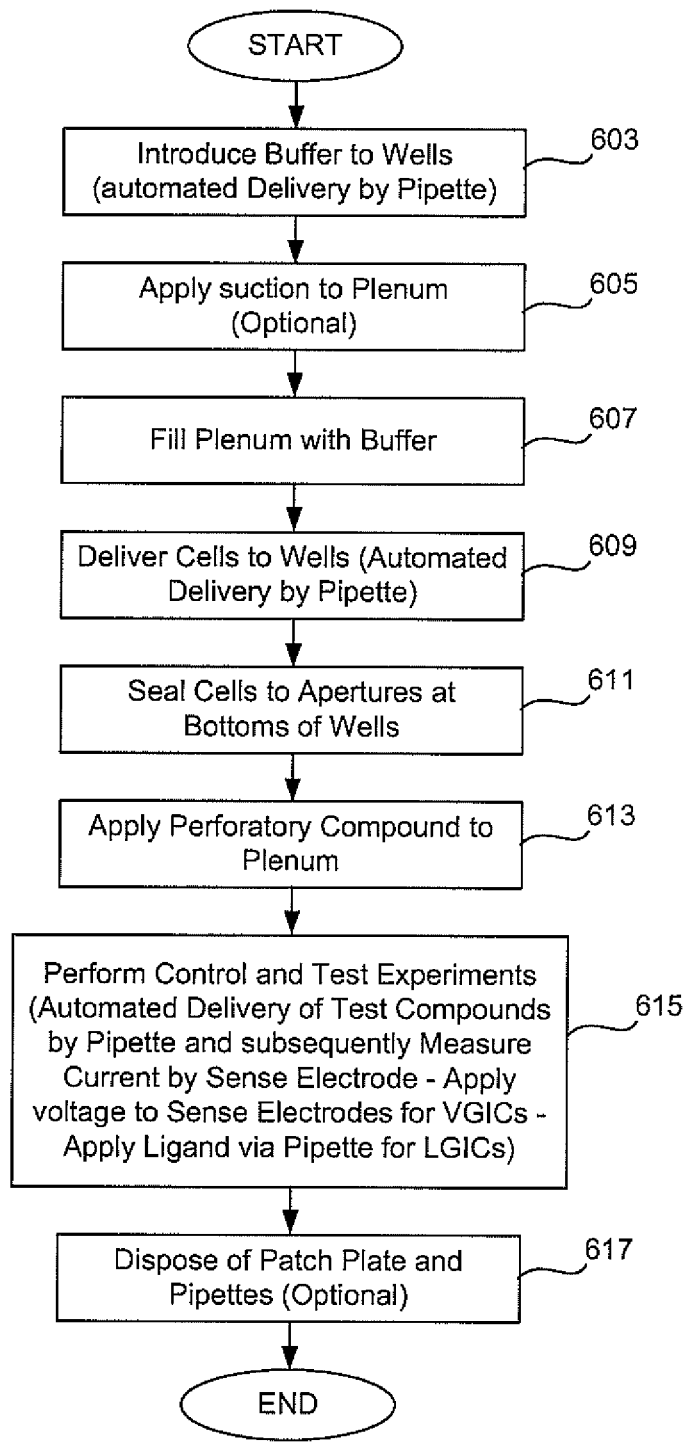
FIG. 6A is a high-level flow chart of a parallel patch clamp process.

For context, FIG. 6A presents a general, high-level, description of a process that would be implemented using any of the above described devices or other devices not specifically presented herein. As depicted in FIG. 6A, the process begins with an operation 603 where the system introduces buffer into the various wells of a multi-well plate such as the patch plate described herein. The buffer may be extracellular buffer for example. The introduction of buffer may be performed by, for example, moving a pipette head such as pipette head 313 shown in FIG. 3 to a buffer reservoir, drawing buffer into each of the pipettes in the pipette head, moving the buffer head over to a patch plate, lowering the pipette head so that the individual pipettes enter the wells of the patch plate, and finally, delivering the buffer from the individual pipettes into the various wells of the patch plate. In embodiments employing an electrode plate or similar template having pipette through holes, the step of lowering the pipette head directs the pipettes through the through holes and into the wells. Once in the wells, the pipettes may contact a pipette guide such as that depicted in FIG. 5A.

After buffer is applied to the individual wells, the process continues with an operation 605 where suction is applied to a plenum below the individual wells in order to clear out any air that may be trapped at the edges of the apertures in the bottom of the wells of the patch plate. Operation 605 is optional and may be unnecessary in certain device designs. Next in the sequence, the plenum below the patch plate is filled with its own buffer solution. See operation 607. Note that the plenum is typically completely filled with buffer so that buffer contacts the bottom surface of the patch plate.

The buffer provided to the plenum may be, for example, an intracellular buffer, which should be contrasted with the extracellular buffer of the type that would be typically introduced into the wells in operation 603. Generally, though not necessarily, the extracellular buffer has a composition chosen to mimic the extracellular environment in which the cells reside in vivo. The intracellular buffer has a composition chosen to mimic that found in the cell interior. For example, the extracellular buffer may contain sodium ions, chloride ions, and calcium ions. The intracellular buffer may have a similar composition, but with a relatively higher concentration of potassium ions and a relatively lower concentration of sodium ions and calcium ions.

After the plenum is completely filled with buffer, the process next involves delivery of cells to the individual wells. This operation is depicted in an operation 609 and may be performed by, for example, automated delivery of cells from a cell reservoir to the individual wells via a pipette head.

After the cells are delivered to the individual wells of the patch plate, the cells are sealed against the apertures on the bottoms of their respective wells. This may be accomplished by establishing a pressure differential between the well and the plenum. This operation is depicted in the flow chart at a block 611. Next, in the sequence, the patch of cell membrane in the apertures is perforated by an appropriate mechanism. In some embodiments, this is accomplished by "zapping" the cells with a relatively high voltage. In other embodiments, as explained above, it is accomplished by introducing a perforatory compound into the plenum. This operation is shown in the flow chart at a block 613. The perforatory compound introduces some degree of perforation into the patch of membrane in the aperture. Typical perforatory compounds are lipophilic compounds including certain antibiotics such as amphotericin. When the perforation is concluded, the device is prepared for conducting a patch clamp assay. Details of the various assays that are performed with the device and its configuration are described in the flow charts of FIGS. 6B and 6C. In FIG. 6A, these assays are generally represented by a block 615. After the assays are completed, the process may optionally involve disposing the pipettes and/or the patch plate, both of which may be contaminated with particular cells or compounds used in the assay. See block 617. Alternatively, the pipettes may also be washed and reused, which is sometimes preferable given that pipettes may be expensive.

As indicated, certain operations may be performed through automated movement of a pipette head. Thus, in accordance with certain embodiments, the operations 603, 609, 615, and 617 of the process depicted in FIG. 6A are performed via automated movement or pipettes. In a specific embodiment, operation 603 involves pipette head 313 moving between station 329 and test region 315. See FIG. 4A. Similarly, operation 609 involves movement between stations 319 and 315, and operation 617 involves movement between stations 323 and 315. Operation 615, which will be described in more detail below, may involve movement between the test region 315 and two or more of the buffer station 329, compound station 325, compound station 327, and wash station 321.

Figure 6B:
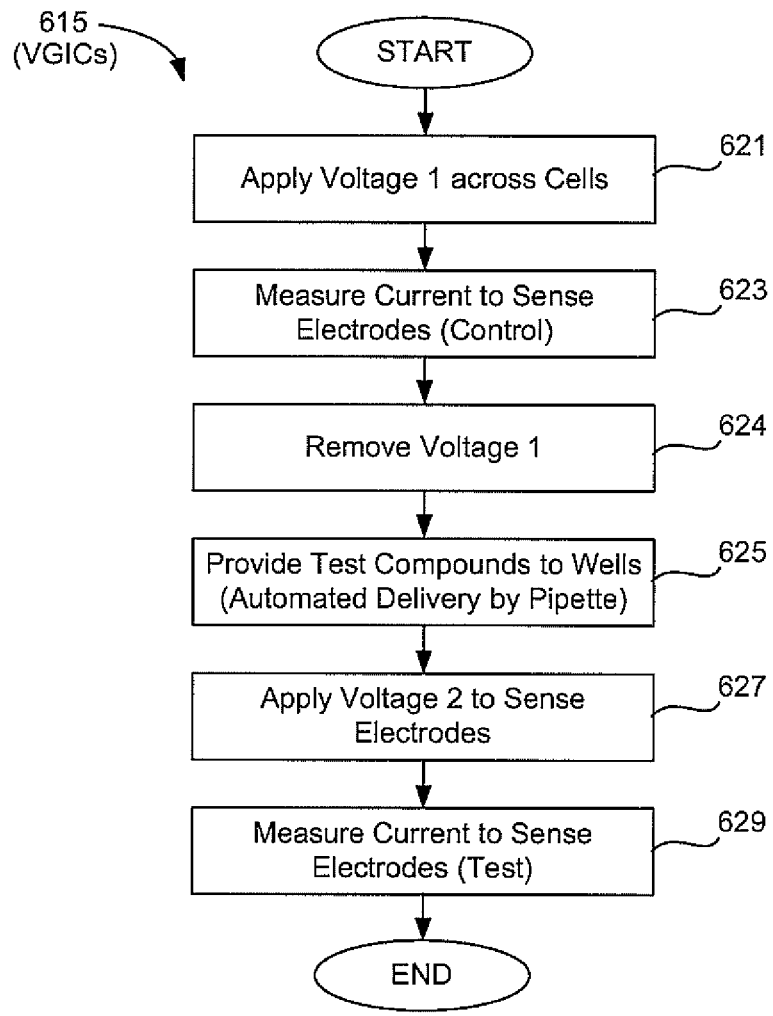
FIG. 6B is a flow chart showing implementation of an assay employing voltage-gated ion channels.

FIG. 6B is a flow chart showing implementation of assay 615 from FIG. 6A, when assay 615 employs voltage-gated ion channels. As shown, the process of FIG. 6B begins with an operation 621 where the instrument control system applies a first voltage between the sense electrode and reference electrode in order to activate a voltage-gated ion channel. This experiment is performed without applying a test compound or other stimulus under investigation. It is intended to obtain a control reading for the operation of the voltage-gated ion channels under consideration. When the instrument applies the first voltage in operation 621, the system concurrently measures current to the sense electrode as shown in an operation 623. This current provides a measure of the control reading for the assay. Next, in an operation 624, the applied voltage is optionally removed. Thereafter, the test compounds or other stimulus under investigation are applied to the individual wells of the patch plate. See block 625. This operation may be performed by an automated delivery using a pipette head. In many assays, different compounds will be applied to the different wells of a patch plate.

The compounds applied in operation 625 may be permitted to incubate for a period of time in order to ensure that their effect is registered by the cells in the assay. Regardless of whether such incubation period is provided, and if it is provided, for how long it is provided, the process continues with re-application of a voltage across the electrodes in order to again trigger opening of the voltage-gated ion channels. See block 627. This voltage may be the same as the voltage applied in operation 621, but it need not be. After the voltage is applied to the electrodes, the circuitry associated with the device again measures the current to the sense electrodes. See block 629. This time, the current value provides a test value, which can be compared against the control value, for the cells in the individual wells. At this point, operation 615 (FIG. 6A) is complete and the process continues with the optional disposal of the patch plate and pipettes as described above.

Figure 6C:
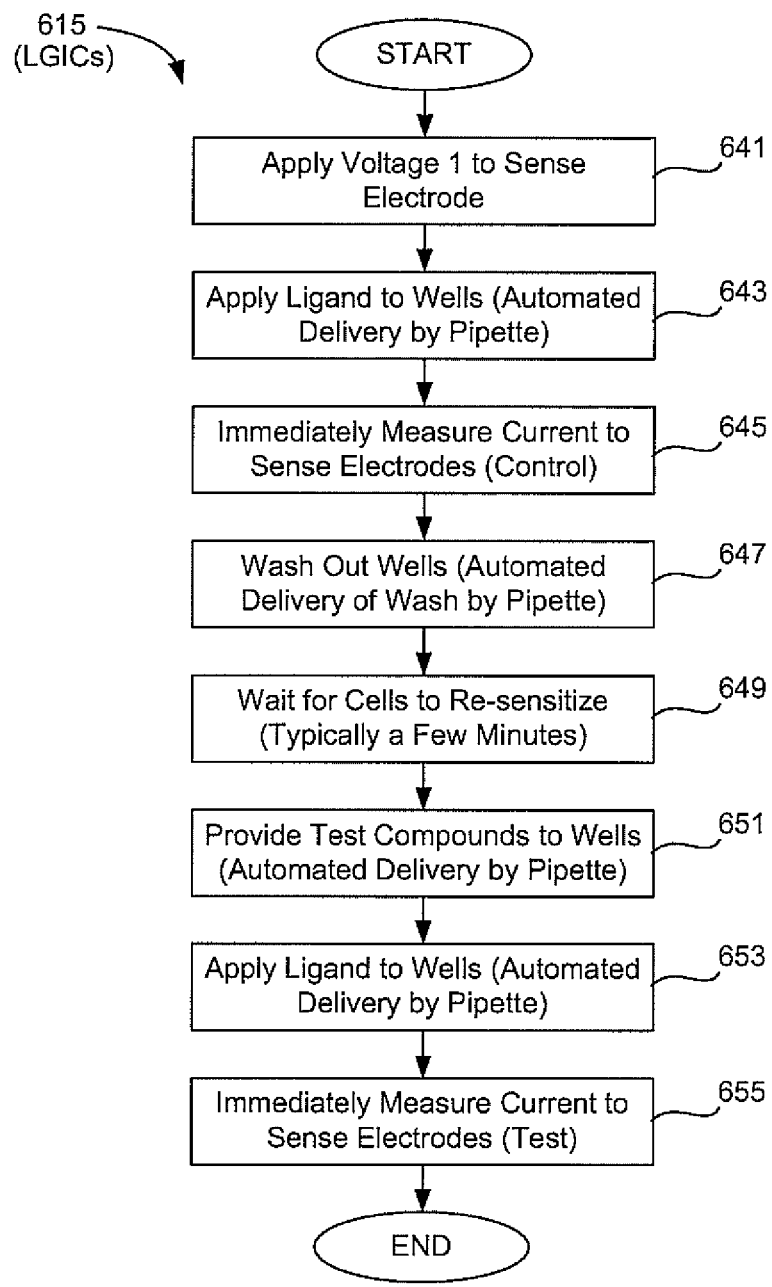
FIG. 6C is a flow chart showing implementation of an assay employing ligand-gated ion channels.

FIG. 6C describes a different implementation of assay 615, an implementation in which ligand-gated ion channels are assayed. As depicted in FIG. 6C, the assay begins with an operation 641 which applies a first voltage across the electrodes in the device. This step may be optional since most ligand-gated ion channels are not activated by voltage, but rather by ligands. If a voltage is applied, it may be of a different value than would be applied to activate a voltage-gated ion channel in a process such as that depicted in FIG. 6B. After optional step 641 is completed, the process continues with application of the required ligand to the individual wells of the patch plate. See block 643. This operation may be performed with an automated pipette head as described above. Note that each of the wells in the patch plate will be given the same ligand because each of them employs cells having the same ligand-gated ion channel. Immediately after the ligand is applied to the wells, the device measures the current to the sense electrodes in order to provide a control measurement for each well. This is depicted in block 645 of FIG. 6C. It is important to immediately measure the current because, as indicated in the discussion of FIG. 2, ligand-gated ion channels quickly become de-sensitized to ligand and "turn off," even in the continued presence of ligand. Note that apparatus of the type described above which employs both a pipette tip and an electrode in a single well permits this immediate measurement of current.

Figure 6D:
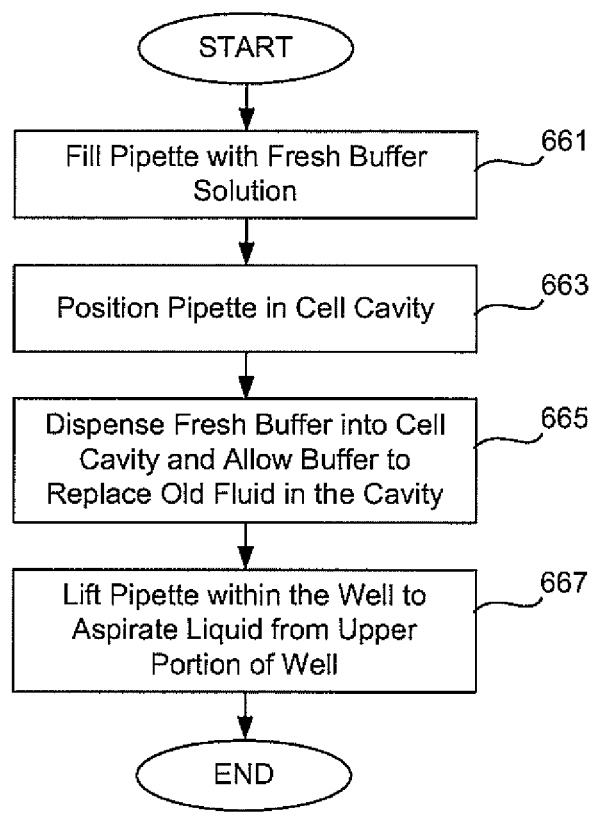
FIG. 6D is a flow chart showing implementation of a well washing process.

After taking the control measurement in operation 645, the process continues with an operation 647 where the individual wells of the patch plate are washed using a buffer or other wash fluid. This process step may be accomplished by automated delivery of wash fluid via pipettes. A specific example of a wash process is depicted in FIG. 6D. After the washing is complete, the process may involve waiting a defined period of time for the cells to re-sensitize so that the next introduction of ligand will again trigger activation of the ion channels. For certain ligand-gated ion channels, this requires waiting a few minutes according to operation 649. During this wait, or afterwards, the instrument applies the test compounds or other stimuli to the individual wells of the patch plate. Again, the compounds or other stimuli may be provided by automated delivery from pipettes. See block 651. Typically, different stimuli are applied to the different wells of the patch plate. Optionally, the cells are incubated with the compounds or other stimuli for a period of time prior to performing test measurements.

When the cells are ready for the test measurements, the process continues with an operation 653 where ligand is applied to each of the wells in the patch plate. As before, the ligand may be provided by an automated delivery from various pipettes. And, as before, after the ligand is delivered to many or all wells, the process continues by immediately measuring the current to the sense electrodes. See operation 655. This current measurement provides test data for comparison against the control data obtained in operation 645. After the test data is obtained and appropriately processed, if necessary, operation 615 from flow chart 6A is completed and the overall process continues as described above.

As should be clear, drug screening, particularly screening for effect on LGICs, often requires repetitive cycles of compound addition and washout. In accordance with certain embodiments, the washout is accomplished as depicted in FIG. 6D. Initially, a pipette is filled with buffer solution (operation 661) and then brought into the well and positioned in the cell cavity. See operation 663. The solution is then dispensed into the bottom cavity, replacing the old fluid in the cavity with the wash fluid (operation 665). Excess solution overflows into the well above the electrode pocket. The pipette may dispense all or most of the buffer it carried into the well. After the pipette empties its contents the fluidics head is lifted up a few millimeters (e.g., about 2-10 mm) so that the tip of the pipette exits the pipette guide and is positioned in the well above the guide (see FIG. 5B) and below the upper level of the fluid within the well. See operation 667. At this point, the action of the fluidic head is reversed and the pipette aspirates the liquid from the top part of the well, leaving behind the clean buffer in the bottom cavity containing the patched cell(s). In other words, the position of the pipette allows it to draw in liquid from an upper region of the well into the pipette. Typically, the pipette tip is raised from the cell cavity within about 0 to 10 seconds after dispensing the buffer or other solution. Note that in some cases, there is no need to wait at all.

The aspirated liquid is a mixture of the old liquid and the wash liquid. This liquid from the pipettes is then dumped into waste, the pipettes are optionally washed/replaced, and the cycles of washout (dispensing wash liquid into the cell cavity through the pipette guide with subsequent lifting of the pipette and aspiration of the mixed liquid from the well above the pipette guide) are repeated sufficient number of times to achieve the required degree of washing.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A multi-well plate comprising:
a plurality of wells, each with a top portion and a bottom portion, wherein at least one well of the multi-well plate has an internal member positioned between the top and bottom portions and the bottom portion of the at least one well comprises:
   (a) a cell cavity formed from its top by a horizontal portion of the internal member and being opened at a through hole within the horizontal portion towards the top portion of the well, sized and shaped to accommodate a pipette tip, and comprising a pipette guide positioned within the horizontal portion of the internal member and shaped and sized for mating with the pipette tip;
   (b) an electrode pocket sized and shaped to accommodate a sensing electrode; and
   (c) a fluidic connection between the cell cavity and electrode pocket, wherein the cell cavity and the electrode pocket are arranged to permit simultaneous accommodation of the pipette tip and the sensing electrode respectively.

2. The multi-well plate of claim 1, wherein the cell cavity comprises at least one cell sealing aperture in a bottom surface of the cell cavity.

3. The multi-well plate of claim 1, wherein the pipette guide shape and size prevents a significant fraction of fluid dispensed from the pipette tip from flowing upward and out of the pipette guide.

4. The multi-well plate of claim 3, the fluidic connection between the cell cavity and the electrode pocket allows for fluid dispensed from the pipette tip to flow primarily into the cell cavity and then through the electrode pocket prior to exiting into an upper region of the well.

5. The multi-well plate of claim 1, wherein the pipette guide is substantially coaxial with a through hole in an electrode plate.

6. The multi-well plate of claim 1, wherein the pipette guide is tapered in the vertical direction.

7. The multi-well plate of claim 1, wherein the height of the electrode pocket, in the vertical direction, is between about 0.2 and 2 mm.

8. The multi-well plate of claim 1, wherein the height of the cell cavity, in the vertical direction, is between about 0.2 and 2 mm.

9. The multi-well plate of claim 1, wherein the diameter or width of the cell cavity is between about 0.5 and 2 mm.

10. The multi-well plate of claim 1, wherein a center-to-center distance between the electrode pocket and the cell cavity is between about 1 and 5 mm.

11. The multi-well plate of claim 1, wherein the cell cavity has a size and shape such that when a pipette tip engages with the cell cavity, said pipette tip comes within about 0.5 mm or less from the bottom of the cell cavity.

12. A method of conducting a patch clamp assay on at least one ligand-gated ion channel, the method comprising:
   (a) sealing a patch of membrane containing the at least one ligand-gated ion channel to the aperture in the cell cavity of the multi-well plate of claim 2;
   (b) delivering a ligand to the well and measuring an electrical signal resulting from exposing the ligand-gated ion channel to the ligand;
   (c) pipetting fresh solution to the bottom of the well from a pipette inserted into the well via the pipette guide to provide a direct fluidic communication between the pipette and the cell cavity via an opening in the cell cavity and to thereby bathe the patch of membrane with the fresh solution;
   (d) moving the pipette within the well and removing old solution containing said ligand from the well;
   (e) applying a stimulus to the patch of membrane; and
   (f) delivering the ligand to the well and measuring an electrical signal resulting from exposing the ligand-gated ion channel to the ligand after application of the stimulus.

13. The method of claim 12, further comprising repeating the sealing of a patch membrane in (a) for a plurality of wells in the multi-well plate.

14. The method of claim 12, further comprising allowing the ligand-gated ion channel to resensitize after (c) and (d) are complete.

15. The method of claim 12, wherein applying the stimulus in (e) comprises applying a pharmaceutically active compound or biological material.

16. The method of claim 12, wherein (b) comprises immediately measuring the electrical signal upon delivering the ligand to the well.

17. The method of claim 12, wherein during (c) the fresh solution is dispensed from the pipette tip and flows primarily into the cell cavity and then through the electrode pocket prior to exiting into an upper region of the well.

18. The method of claim 17, wherein the pipette guide is substantially coaxial with a corresponding through hole in an electrode plate disposed above the well.

19. The method of claim 17, wherein the pipette guide is tapered in the vertical direction.

20. The method of claim 17, wherein a height of the cell cavity, in the vertical direction, is between about 0.2 and 2 mm.

* * * * *